United States Patent [19]

Colclough

[11] Patent Number: 5,739,089
[45] Date of Patent: Apr. 14, 1998

[54] DIHYDROCARBYL DITHIOPHOSPHATES

[75] Inventor: Terence Colclough, Abingdon, United Kingdom

[73] Assignee: Exxon Chemical Patents Inc., Linden, N.J.

[21] Appl. No.: 814,208

[22] Filed: Mar. 11, 1997

Related U.S. Application Data

[62] Division of Ser. No. 938,305, Aug. 28, 1992, which is a continuation of Ser. No. 274,819, Nov. 22, 1988, abandoned.

[51] Int. Cl.$^6$ .................................................. C10M 137/06
[52] U.S. Cl. .................................................. 508/368
[58] Field of Search .................................................. 508/368

[56] References Cited

U.S. PATENT DOCUMENTS

| | | | |
|---|---|---|---|
| 2,364,283 | 12/1944 | Freuler | 252/37 |
| 2,364,284 | 12/1944 | Freuler | 252/39 |
| 2,552,570 | 5/1951 | McNab et al. | 252/32.7 |
| 2,618,597 | 11/1952 | McNab et al. | 252/32.7 |
| 2,737,492 | 3/1956 | Beegle et al. | 252/32.7 |
| 3,014,940 | 12/1961 | Lynch et al. | 260/429 |
| 3,210,275 | 10/1965 | Durr, Jr. | 252/32.7 |
| 3,347,790 | 10/1967 | Meinhardt | 252/32.5 |
| 3,360,463 | 12/1967 | Jacques | 252/32.7 |
| 3,376,221 | 4/1968 | Butler | 252/32.7 |
| 3,401,185 | 9/1968 | Meinhardt | 260/429.9 |
| 3,423,316 | 1/1969 | Dickert, Jr. et al. | 252/32.7 |
| 3,481,716 | 12/1969 | Mrstik et al. | 44/68 |
| 3,523,081 | 8/1970 | Braid | 252/32.7 |
| 3,595,792 | 7/1971 | Elliott et al. | 508/368 |
| 4,203,854 | 5/1980 | Silverstein | 252/25 |
| 4,259,192 | 3/1981 | Lilburn | 252/32.7 E |
| 4,308,154 | 12/1981 | Clason et al. | 252/32.7 |
| 4,392,966 | 7/1983 | Schlicht | 252/32.7 E |
| 4,466,895 | 8/1984 | Schroeck | 508/368 |
| 4,582,920 | 4/1986 | Bridger | 556/25 |
| 4,664,822 | 5/1987 | Hunt | 252/37.7 E |
| 4,707,284 | 11/1987 | Goldblatt et al. | 252/32.7 |
| 4,764,294 | 8/1988 | Habeeb et al. | 252/32.7 |
| 4,767,551 | 8/1988 | Hunt | 252/32.7 E |

FOREIGN PATENT DOCUMENTS

| | | |
|---|---|---|
| 0024146 | 8/1980 | European Pat. Off. . |
| 0131400 | 6/1984 | European Pat. Off. . |
| 2056482 | 8/1979 | United Kingdom ............ C10M 1/48 |
| 8605492 | 3/1986 | WIPO . |
| 8606378 | 4/1986 | WIPO . |

*Primary Examiner*—Jacqueline V. Howard
*Attorney, Agent, or Firm*—Ohlandt, Greeley, Ruggiero & Perle

[57] ABSTRACT

A mixed zinc/copper dihydrocarbyl dithiophosphate, e.g. of zinc diethyl-hexyl dithiophosphate and cuprous diethylhexyl dithiophosphate, is prepared by reacting a dihydrocarbyl dithiophosphoric acid (DDPA) with a mixture of a basic zinc compound eg ZnO, and a basic copper compound eg $Cu_2O$, preferably in the presence of a promoter, eg zinc acetate. The product is a good antioxidant for use in lubricating oils.

15 Claims, No Drawings

DIHYDROCARBYL DITHIOPHOSPHATES

This is a divisional, of application Ser. No. 07/938,305, filed Aug. 28, 1992, which is a continuation of application Ser. No. 07/274,819 filed Nov. 22, 1988, now abandoned.

This invention relates to a process for making dihydrocarbyl dithiophosphates and their use as lubricating oil additives.

Zinc dihydrocarbyl dithiophosphates have been used for years as antiwear and antioxidant additives in lubricating oils. For example, EP 0024146 discloses lubricating oil compositions comprising specified amounts of ashless dispersant and/or viscosity index improver dispersant, zinc dihydrocarbyl dithiophosphate and added copper present as an oil soluble copper compound. It has been suggested that copper dialkyl dithiophosphates are potent antioxidants. However, the copper species has a lower hydrogen sulphide stability compared with the zinc species. Mixtures of zinc, copper and iron dialkyl dithiophosphates have been proposed, see for example U.S. Pat. No. 4,466,895.

From the economic point of view it is highly desirable to use dialkyl dithiophosphates where the alkyl groups contain less than 6 carbon atoms. However, copper dialkyl dithiophosphates, particularly when the alkyl group contains less than about 6 carbon atoms, tend to be solid and/or insoluble in hydrocarbons such as lubricating oil base stocks and/or exhibit poor copper corrosion properties when used alone. We have now discovered a method of making mixed copper and zinc dihydrocarbyl dithiophosphates which are liquid with good oil solubility and good copper corrosion inhibition.

According to this invention a mixed zinc/copper dihydrocarbyl dithiophosphate (hereinafter referred to as Zn/Cu DDP) is prepared by a process comprising reacting a dihydrocarbyl dithio phosphoric acid with a mixture of a basic zinc compound and a basic copper compound. This invention also provides the use in a lubricating oil of the mixture.

The general formula of the dihydrocarbyl dithio phosphoric acid from which Zn/Cu DDP is derived is

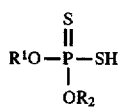

where $R^1$ and $R^2$ are similar or different and are hydrocarbyl groups.

The groups $R^1$ and $R^2$ preferably contain from 1 to 18 carbon atoms. They may be alkyl, alkenyl, aryl, aralkyl, alkaryl or cycloaliphatic radicals, but they are preferably alkyl or alkaryl radicals. Particularly preferred are $C_2$ and $C_{10}$ alkyl groups especially $C_2$ to $C_6$ alkyl groups eg ethyl, n-propyl, i-propyl, n-butyl, i-butyl, sec-butyl, amyl, n-hexyl, n-heptyl, n-octyl, i-octyl, 4-methylpent-2-yl, 2-ethylhexyl and n-decyl. Mixtures can be used eg $R^1$ butyl and $R^2$ amyl. Other preferred examples are $C_{14}$ to $C_{20}$ alkaryl groups, eg nonyl phenyl, decylphenyl and dodecylphenyl. The alkyl groups or alkyl portion of the alkaryl or aralkyl groups can be straight chain or branched.

The dihydrocarbyl dithiophosphoric acid is reacted with a mixture of a basic zinc compound and a basic copper compound. The reactants are preferably the oxides or hydroxides but they can be other salts of zinc and copper provided that the anion can be replaced by the anion of the dihydrocarbyl dithiophosphoric acid. Cuprous oxide is preferred to cupric oxide and cupric hydroxide. Other basic zinc and basic copper compounds which may be used are preferably soluble in the dihydrocarbyl dithiophosphoric acid. Examples of other suitable basic salts of zinc and copper are the carboxylates, eg stearates, acetates and carbonates.

The ratio of basic zinc compound to basic copper compound is not fixed and can vary over wide limits. Generally, the weight ratio of zinc to copper in the product Zn/Cu DDP should preferably be from 30:1 to 1:30, especially between 10:1 and 1:10 and most preferably between 10:1 and 1:1.

When neutralising the dihydrocarbyl dithiophosphoric acid with the mixture of basic zinc compound and basic copper compound it is preferred to use a promoter. Suitable promoters are carboxylic acids, metal carboxylates and other metal salts, particularly the carboxylates and other salts of zinc and copper, eg nitrates, phosphates, sulphates or halides. Especially preferred are the zinc salts, particularly zinc carboxylates, zinc chloride, zinc phosphate, zinc nitrate and zinc sulphide. The preferred carboxylic acids for use as such or as their carboxylates are $C_1$ and $C_{20}$ monocarboxylic acids, eg acetic acid, propionic acid, decanoic acid, stearic acid and oleic acid and dicarboxylic acids such as substituted succinic acids. The most preferred promoter is zinc acetate.

The amount of promoter used is usually less than 10 weight %, for example between 0.1 and 10 weight % of the total weight of the basic zinc compound.

The Zn/Cu DDP is simply prepared by heating together the dihydrocarbyl dithiophosphoric acid with the mixture of basic zinc and basic copper compounds and if used, the promoter. The acid may be slowly added to the basic zinc and copper compounds which are generally used in the form of a slurry, for example with mineral oil. Alternatively, the basic zinc and copper compounds, and promoter if used, are added to about half the acid and then the remainder of the acid added. Since there is a tendency for the copper compound to react preferentially with the acid, in a preferred aspect the zinc and copper compounds are introduced separately into the reaction mixture with at least a part of the zinc compound being introduced first to ensure basic Zn DDP is formed. Thus, in either sequence described above, some or all of the zinc compound is combined with the acid, then copper compound is introduced and any remaining zinc compound is added with or after the copper compound. The reactants are usually heat soaked eg at 40° C. to 60° C. and then heated to a temperature of between 60° C. and 100° C. for example about 85° C. and the remainder of the acid added, if only some acid has been used hitherto. As indicated above the zinc and/or copper compounds may be slurried in a liquid vehicle, for example a mineral oil or a residual amount of ZnDDP or of Zn/Cu DDP, before reacting with the acid. The amount of diluent oil vehicle can be quite low, for example 5–10% of the total reaction mixture and it is advantageous to use small amounts because this results in lower treat rates when the Zn/Cu DDP is used as a lubricating oil additive.

After maintaining the reactants at the reaction temperature for 1 to 4 hours, eg about 1.0 to 3.0 hours the reaction mixture is preferably cooled, flocculant is added and the mixture is stripped and filtered. The filtrate is the desired product.

The Zn/Cu DDP when used as a lubricating oil additive has good copper corrosion inhibition properties. These properties are improved if the dihydrocarbyl dithiophosphoric acid is derived from a phosphorus pentasulphide having substantially no free sulphur present and hence a high phosphorus content. Improved copper corrosion lubrication properties have been obtained by using a grade of phosphorus pentasulphide having a phosphorus content of 27.9±0.1 weight %, compared with the usual commercial grade which has 27.6±0.2 weight % of phosphorus. However it is a surprising feature of the Zn/Cu DDP of the invention that better copper corrosion properties are seen with such commercial grades of $P_2S_5$ than would be expected from simple Zn DDP.

Better thermal and hydrolytic stabilities are obtained when using the Zn/Cu DDP in a lubricating oil if the Zn DDP component has a higher Zn/P ratio than is normal, eg 1.14 to 1.25 compared with 1.10. This is achieved by using excess basic zinc compound, eg zinc oxide or hydroxide over stoichiometric up to a level where too much sedimentation would occur.

The products of the invention have excellent copper corrosion properties. Further improvement in copper corrosion properties of the Zn/Cu DDP and improvement in product colour may be obtained by treatment with one or more phosphites to the formed Zn/Cu DDP. Preferred phosphites are triphenyl, tributyl, tris(2-ethylhexyl) and tris (alkylphenyl) phosphites. Preferred amounts are 1 to 5 wt % based on the weight of Zn/Cu DDP.

The lubricating oil to which the Zn/Cu DDP can be added includes mineral lubricating oils and synthetic lubricating oils and mixtures thereof. The synthetic oils include poly-alpha olefins, diester oils such as di(2-ethylhexyl) sebacate, azelate and adipate, complex ester oils such as those formed from dicarboxylic acids, glycols and either monobasic acids or monohydric alcohols and silicone oils.

The lubricating oil base stock for the antioxidant additives of the present invention typically is adapted to perform a selected function by the incorporation of additives therein to form lubricating oil compositions (i.e. formulations).

Representative additives typically present in such formulations include viscosity modifiers, corrosion inhibitors, oxidation inhibitors, friction modifiers, dispersants, anti-foaming agents, anti-wear agents, pour point depressants, detergents, rust inhibitors and the like.

Viscosity modifiers impart high and low temperature operability to the lubricating oil and permit it to remain shear stable at elevated temperatures and also exhibit acceptable viscosity or fluidity at low temperatures.

Viscosity modifiers are generally high molecular weight hydrocarbon polymers including polyesters. The viscosity modifiers may also be derivatized to include other properties or functions, such as the addition of dispersancy properties.

These oil soluble viscosity modifying polymers will generally have number average molecular weights of from $10^3$ to $10^6$, preferably $10^4$ to $10^6$, e.g., 20,000 to 250,000, as determined by gel permeation chromatography or membrane osmometry.

Representative examples of suitable viscosity modifiers are any of the types known to the art including polyisobutylene, copolymers of ethylene and propylene, polymethacrylates, methacrylate copolymers, copolymers of an unsaturated dicarboxylic acid and vinyl compound, interpolymers of styrene and acrylic esters, and styrene/isoprene copolymers.

Corrosion inhibitors, also known as anti-corrosive agents, reduce the degradation of the metallic parts contacted by the lubricating oil composition. Illustrative of corrosion inhibitors are phosphosulphurized hydrocarbons and the products obtained by reaction of a phosphosulphurized hydrocarbon with an alkaline earth metal oxide or hydroxide, preferably in the presence of an alkylated phenol or of an alkylphenol thioester, and also preferably in the presence of carbon dioxide. Phosphosulphurized hydrocarbons are prepared by reacting a suitable hydrocarbon such as terpene, a heavy petroleum fraction of a $C_2$ to $C_6$ olefin polymer such as polyisobutylene, with from 5 to 30 wt. % of a sulfide of phosphorus for ½ to 15 hours, at a temperature in the range of 150° to 600° F. Neutralization of the phosphosulphurized hydrocarbon may be effected in the manner taught in U.S. Pat. No. 1,969,324.

Oxidation inhibitors reduce the tendency of mineral oils to deteriorate in service which deterioration can be evidenced by the products of oxidation such as sludge and varnish-like deposits on the metal surfaces and by viscosity growth. Such oxidation inhibitors include ZDDP's aromatic amines such as alkylated diphenylamines and phenyl alphanaphthylamines, hindered phenols, copper compounds, alkaline earth metal salts of alkylphenolthioesters having preferably $C_5$ to $C_{12}$ alkyl side chains, eg, calcium nonylphenol sulphide, barium t-octylphenyl sulphide, dioctylphenyl-amine, phenylalphanaphthylamine, phosphosulphurized or sulphurized hydrocarbons, etc.

Friction modifiers serve to impact the proper friction characteristics to lubricating oil compositions such as automatic transmission fluids.

Representative examples of suitable friction modifiers are found in U.S. Pat. No 3,933,659 which discloses fatty acid esters and amides; U.S. Pat. No. 4,176,074 which describes molybdenum complexes of polyisobutenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses S-carboxyalkylene hydrocarbyl succinimide, s-carboxyalkylene hydrocarbyl succinamic acid and mixtures thereof; U.S. Pat. No. 3,879,306 which discloses N-(hydroxyalkyl)alkenyl-succinamic acids or succinimides; U.S. Pat. No. 3,932,290 which discloses reaction products of di-(lower alkyl) phosphites and epoxides; and U.S. Pat. No. 4,028,258 which discloses the alkylene oxide adduct of phosphosulphurized N-(hydroxyalkyl) alkenyl succinimides. The disclosures of the above references are herein incorporated by reference. The most preferred friction modifiers are succinate esters, or metal salts thereof, of hydrocarbyl substituted succinic acids or anhydrides and thiobis alkanols such as described in U.S. Pat. No. 4,344, 853.

Dispersants maintain oil insolubles, resulting from oxidation during use, in suspension in the fluid thus preventing sludge flocculation and precipitation or deposition on metal parts. Suitable dispersants include high molecular weight alkenyl succinimides, the reaction product of oil-soluble polyisobutylene succinic anhydride with ethylene amines such as tetraethylene pentamine and borated salts thereof.

Pour point depressants lower the temperature at which the fluid will flow or can be poured. Such depressants are well known. Typically of those additives which usefully optimize the low temperature fluidity of the fluid are $C_8$–$C_{18}$ dialkylfumarate vinyl acetate copolymers, polymethacrylates, and wax naphthalene. Foam control can be provided by an antifoamant of the polysiloxane type, eg, silicone oil and polydimethyl siloxane.

Detergents and metal rust inhibitors include the metal salts of sulphonic acids, alkyl phenols, sulphurized alkyl phenols, alkyl saliscylates, naphthenates and other oil soluble mono- and di-carboxylic acids.

Highly basic (viz, overbased) metals salts, such as highly basic alkaline earth metal sulphonates (especially Ca and Mg salts) are frequently used as detergents.

Copper corrosion inhibitors and antiwear agents include borate ester, thiadiazoles such as derivatives of 2,5 dimercapto 1,3,4-thiadiazole and benzotriazoles.

Some of these numerous additives can provide a multiplicity of effects, eg a dispersant-oxidation inhibitor. This approach is well known and need not be further elaborated herein.

Compositions when containing these conventional additives are typically blended into the base oil in amounts which are effective to provide their normal attendant function. Representative effective amounts of such additives are illustrated as follows:

| Additive | Vol % | Wt % a.i. |
| --- | --- | --- |
| Viscosity Modifier | .01–4 | .01–4 |
| Corrosion Inhibitor | 0.01–1 | .01–1.5 |
| Oxidation inhibitor | 0.01–1 | .01–1.5 |
| Dispersant | 0.1–7 | 0.1–8 |
| Pour Point Depressant | 0.01–1 | .01–1.5 |
| Anti-Foaming Agents | 0.001–0.1 | .001–0.15 |
| Anti-Wear Agents | 0.001–1 | .001–1.5 |
| Friction Modifiers | 0.01–1 | .01–1.5 |
| Detergents/Rust Inhibitors | .01–2.5 | .01–3 |
| Mineral Oil Base | Balance | Balance |

When other additives are employed, it may be desirable, although not necessary, to prepare additive concentrates comprising concentrated solutions or dispersions of the dispersant (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The concentrate or additive-package will typically be formulated to contain the dispersant additive and optional additional additives in proper amounts to provide the desired concentration in the final formulation when the additive-package is combined with a predetermined amount of base lubricant. Thus, the dispersant of the present invention can be added to small amounts of base oil or other compatible solvents along with other desirable additives to form additive-packages containing active ingredients in collective amounts of typically from about 2.5 to about 90%, and preferably from about 5 to about 75%, and most preferably from about 8 to about 50% by weight additives in the appropriate proportions with the remainder being base oil.

The final formulations may employ typically about 10 wt. % of the additive-package with remainder being base oil.

All of said weight percents expressed herein are based on active ingredient (a.i.) content of the additive, and/or upon the total weight of any additive-package, or formulation which will be the sum of the a.i. weight of each additive plus the weight of total oil or diluent.

The amount of the mixture of Zn/Cu DDP added to the lubricating oil is a minor proportion by weight, preferably less than 20% by weight, more preferably 0.2 to 2.0 and especially 0.5 to 1.5 % by weight.

Additives for lubricating oils are generally supplied as concentrates in solvent (eg oil) for incorporation into the bulk lubricant. According to this invention a concentrate comprises a solvent and 20 to 90 weight % of the Zn/Cu DDP obtained by the process of this invention. Suitable solvents include kerosene, aromatic naphthas, mineral lubricating oils etc. Such concentrates may contain one or more other lubricant additives such as described above to form a package which may be diluted with lubricant basestock to form a lubricating oil composition.

EXAMPLE 1

Zn/Cu DDP was prepared as follows: The following charge quantities were used

Bis 2-ethylhexyldithiophosphoric acid

| (DDPA) | 200 g |
| --- | --- |
| Cuprous oxide | 6.4 g |
| Zinc oxide | 33.5 g |
| Zinc acetate | 1.0 g |

The cuprous oxide followed by the zinc oxide and zinc acetate were added to 100 g of the DDPA at 50° C. After a heat soak for 30 minutes, the temperature was raised to 85° C. and the remainder of the acid was added. The product was flocculated, stripped and filtered.

The 100% active ingredient product had the following analysis Zn:8.0 wt %, Cu:1.6 wt %, P:7.9 wt % and S:14.7 wt %.

It can be seen that a blend of the Zn/Cu DDP at a phosphorus concentration of 0.1% P would provide a concentration of copper of 200 ppm.

The Zn/Cu DDP obtained was subjected to a $H_2S$ stability test which involved heating Zn/Cu DDP at 135° C. in the presence of 3% water and measuring the time to $H_2S$ evolution, which is the result quoted in the test.

The $H_2S$ stability of this Zn/Cu DDP was found to be excellent (7+ hours at 135° C.).

EXAMPLE 2

| DDPA charge quantities: | iso-butanol | 428 g |
| --- | --- | --- |
| | iso-amyl alcohol | 231 g |
| | $P_2S_5$ | 444 g |

All of the $P_2S_5$ was charged to the reaction pot. 165 g of the alcohol mixture were added with stirring. The temperature rose from 23° to 80° C. After 20 minutes heat soak the temperature was increased to 85° C. and the remainder (494 g) of alcohol mixture was added over 2 hours, followed by a 2 hour heat soak at 85° C. The acid had 12.1%P.

| Cu/Zn DDP charge quantities: | DDPA | 900 g |
| --- | --- | --- |
| | ZnO | 135 g |
| | $Cu_2O$ | 26.3 g |

The pot was charged with 309 g acid and all the ZnO and $Cu_2O$ were added over 15 mins. The temperature rose from 20° to 80° C. The reaction mixture was heat soaked for 30 mins. and then the rest of the acid was added over 2 hours at 85° C. After 30 mins. heat soak the mixture was worked up to give a brown haze-free liquid product.

This Cu/Zn DDP had an $H_2S$ stability of 30 minutes.

1% of this product was dissolved in a mineral oil and tested in the ASTM D-130 copper corrosion test at 100° and 150° C. A 1A rating was obtained in both cases, i.e. excellent (no corrosion).

A treatment with 1% and 2% triphenyl phosphite at 100° C. changed the colour from dark brown to light brown.

The Cu/Zn DDP thus obtained was subjected to the CEC Rig Scuffing Test (CEC L-31-T-81) and compared with Zn DDP derived from primary $C_4$ and $C_5$ alcohols, both at 0.1 wt % P concentration. From the data given below it can be seen that the mixed Cu/Zn DDP has excellent scuffing activity.

CEC Rig Scuffing Test (CEC L-31-T-81)

| Oil Contains: | | | |
|---|---|---|---|
| Multifunctional VI | 8.5 | 8.5 | 8.5 |
| Mg high base number sulphonate detergent | 1.6 | 1.6 | 1.6 |
| Succinimide dispersant | 3.0 | 3.0 | 3.0 |
| Zn DDP (primary $C_4/C_5$) | 1.3 | — | — |
| Cu/Zn DDP (primary $C_4/C_5$) | — | 0.9 | — |
| 150 Neutral base oil | 85.6 | 86.0 | 86.9 |
| % P in oil | 0.1 | 0.1 | — |
| Cam & Tappet wt loss (mg) | 46.0 | 11.0 | 6000+ |

EXAMPLE 3

In order to improve the rather low $H_2S$ stability obtained in the previous preparation (Example 2), three changes were made: The Zn/P ratio was increased; Zn acetate was added as neutralization promoter; ZnO and Zn acetate were added before the $Cu_2O$. These changes were designed to increase the basic Zn content and so improve the $H_2S$ stability and this was achieved.

| Charge qualities: | DDPA | 300 g |
|---|---|---|
| | ZnO | 46.6 g |
| | Zn Acetate | 1.4 g |
| | $Cu_2O$ | 9.2 g |

The pot was charged with 102 g of the acid. All the ZnO and Zn acetate were added over 5 mins. The temperature rose from 18° to 62° C. The mixture was heat soaked for 30 mins. and the temperature then raised to 85° C. All the cuprous oxide was then added quickly, followed by the remainder of the acid over 1.5 hours. After 1 hour heat soak, the mixture was worked up to give a brown haze-free liquid product.

Analysis: Zn 11.8; Cu 2.2; P 11.2; S 21.8%

The Cu/Zn DDP had good $H_2S$ stability (3.25 hrs/135° C.) and good copper corrosion properties (1A) both at 100° and 150° C.

Treatment of the product with triphenyl phosphite (2 and 3%) at 100° C., improved the colour without affecting the copper corrosion properties or $H_2S$ stability.

This product Zn/Cu DDP was then tested in a bench oxidation test and compared with a conventional Zn DDP at equal phosphorus treat levels (0.1%P). The Zn DDP was made in a similar manner to the above except that no cuprous oxide was used. The oxidation test consists of heating a 300 g sample of the lubricating oil blend containing the Zn/Cu DDP or the Zn DDP for 64 hours at 165° C. Air was passed through the blend at the rate of 1.7 liters per hour and ferric acetyl acetonate was present at the level of 40 ppm soluble iron to act as oxidation catalyst. Samples were taken at intervals up to 64 hours, and the viscosity measured at 40° C. by means of a cone-on-plate viscometer. The results are shown below:

| | | | |
|---|---|---|---|
| Ethylene/propylene copolymer viscosity modifier | 7.9 | 7.9 | mass % |
| Polyisobutenyl succinimide dispersant | 4.5 | 4.5 | |
| Mg high base number sulphonate (TBN = 400) | 1.0 | 1.0 | |
| Zn DDP (primary $C_4/C_5$) | 1.3 | — | |
| Zn/Cu DDP ((primary $C_4/C_5$) | — | 0.9 | |
| S150 neutral basestock | 85.3 | 85.7 | |

Viscosity cP at hours

| | | |
|---|---|---|
| 0 | 65 | 63 |
| 16 | 115 | 58 |
| 24 | 208 | 61 |
| 40 | solid | 81 |
| 48 | | 110 |
| 64 | | 156 |

It can be seen that the Zn/Cu DDP is a much more powerful antioxidant than the Zn DDP and it is to be expected the oil containing the Zn/Cu DDP would pass the Sequence III D test whereas the oil containing the Zn DDP would fail.

EXAMPLE 4

The procedure of Example 3 was repeated on a larger scale.

| Charge quantities: | DDPA | 1000.0 g |
|---|---|---|
| | ZnO | 154.9 g |
| | Zn acetate | 4.7 g |
| | $Cu_2O$ | 30.6 g |

The product analysis was Zn=11.0, Cu=2.1, P=9.6, S=17.5.

The $H_2S$ stability was 2 hrs/135° C.

EXAMPLE 5

| Charge quantities: | $C_4/C_5$ acid (DDPA) | 300.0 g |
|---|---|---|
| | ZnO | 46.5 g |
| | Zn acetate | 1.4 g |
| | Cupric oxide | 5.1 g |

The pot was charged with 74 g acid. All of the ZnO and Zn acetate was added over 5 mins., and the reaction was exothermic (the temperature rising from 26° to 56° C.). The product was soaked for 30 mins., the temperature was raised to 85° C. CuO was added quickly, followed by the rest of DDPA over 100 mins. The product was heat soaked for 80 mins. and then worked up to give a brown haze-free liquid product.

$H_2S$ Stability 30 mins.

Zn 11.6 Cu 0.7 P 10.9 S 21.1 wt %

In the copper corrosion test according to the ASTM D130 test at 150° C. this product gave a 1A rating confirming that it had excellent copper corrosion properties. Treatment with 3% triphenyl phosphite improved the colour of the product.

I claim:

1. A lubricating oil composition comprising a lubricating oil and 0.2 to 2.0% by weight of an oil-soluble, liquid, mixed zinc and copper dihydrocarbyl dithiophosphate, wherein the hydrocarbyl groups are alkyl of up to six carbon atoms and the mixed dithiophosphate is prepared by a process in which dihydrocarbyl dithiophosphoric acid is reacted with a mixture of a basic zinc compound and a basic copper compound selected from the group consisting of copper oxide and copper hydroxide.

2. A lubricating oil composition as claimed in claim 1 wherein the weight ratio of zinc to copper is from 10:1 to 1:1.

3. A lubricating oil composition as claimed in claim 2 wherein the dihydrocarbyl dithiophosphoric acid is derived from a phosphorus pentasulfide having 27.9±0.1 weight % of phosphorus.

4. A lubricating oil composition as claimed in claim 2 wherein the dihydrocarbyl groups of the mixed zinc and copper dihydrocarbyl dithiophosphate are 2-ethylhexyl groups.

5. A lubricating oil composition as claimed in claim 2 wherein the dihydrocarbyl groups of the mixed zinc and copper dihydrocarbyl dithiophosphate comprise an iso-butyl and an iso-amyl group.

6. A concentrate comprising a solvent and from 20 to 90% by weight of an oil-soluble, liquid, mixed zinc and copper dihydrocarbyl dithiophosphate, wherein the hydrocarbyl groups are alkyl of up to six carbon atoms and the mixed dithiophosphate is prepared by a process in which dihydrocarbyl dithiophosphoric acid is reacted with a mixture of a basic zinc compound and a basic copper compound selected from the group consisting of copper oxide and copper hydroxide.

7. A concentrate as claimed in claim 6 wherein the weight ratio of zinc to copper is from 10:1 to 1:1.

8. A concentrate as claimed in claim 7 wherein the dihydrocarbyl dithiophosphoric acid is derived from a phosphorus pentasulfide having 27.9±0.1 weight % of phosphorus.

9. A concentrate as claimed in claim 6 wherein the dehydrocarbyl groups of the mixed zinc and copper dehydrocarbyl dithiophosphate are 2-ethylhexyl groups.

10. A concentrate as claimed in claim 7 wherein the dihydrocarbyl groups of the mixed zinc and copper dihydrocarbyl dithiophosphate comprise an iso-butyl and an iso-amyl group.

11. A process of providing improved antioxidant and copper corrosion inhibition to a lubricating oil composition comprising adding to a lubricating oil from 0.2 to 2.0% by weight of an oil-soluble, liquid, mixed zinc and copper dihydrocarbyl dithiophosphate, wherein the hydrocarbyl groups are alkyl of up to six carbon atoms and the mixed dithiophosphate is prepared by a process in which dihydrocarbyl dithiophosphoric acid is reacted with a mixture of a basic zinc compound and a basic copper compound selected from the group consisting of copper oxide and copper hydroxide.

12. A process a claimed in claim 11 wherein the weight ratio of zinc to copper is from 10.1 to 1:1.

13. A process as claimed in claim 11 wherein the dihydrocarbyl dithiophosphoric acid is derived from a phosphorus pentasulfide having 27.9±0.1 weight % of phosphorus.

14. A process as claimed in claim 12 wherein the dihydrocarbyl groups of the mixed zinc and copper dihydrocarbyl dithiophosphate are 2-ethylhexyl groups.

15. A process as claimed in claim 12 wherein the dihydrocarbyl groups of the mixed zinc and copper dehydrocarbyl dithiophosphate comprise an iso-butyl and an iso-amyl group.

* * * * *